US009464132B2

(12) United States Patent
Zigangirova et al.

(10) Patent No.: US 9,464,132 B2
(45) Date of Patent: Oct. 11, 2016

(54) **NANOANTIBODIES, BINDING *CHLAMYDIA TRACHOMATIS* ANTIGEN, METHOD FOR INHIBITION OF INFECTION INDUCED BY *CHLAMYDIA TRACHOMATIS***

(71) Applicant: Obschestvo s ogranichennoi otvetstvennostyu "Tekhnopharma", selo Glebovskoe, Pereslavsky raion (RU)

(72) Inventors: Nailya A. Zigangirova, Moscow (RU); Sergey V. Tillib, Moscow (RU)

(73) Assignee: Obschestvo s ogranichennoi otvetstvennostyu "Tekhnopharma", selo Glebovskoe, Yaroslavskaya obl. (RU)

(*) Notice: Subject to any disclaimer, the term of this patent is extended or adjusted under 35 U.S.C. 154(b) by 0 days.

(21) Appl. No.: 14/334,736

(22) Filed: Jul. 18, 2014

(65) Prior Publication Data

US 2014/0329320 A1 Nov. 6, 2014

Related U.S. Application Data

(63) Continuation of application No. PCT/RU2013/000227, filed on Mar. 19, 2013.

(30) Foreign Application Priority Data

Jan. 20, 2012 (RU) ................................ 2012101955

(51) Int. Cl.
*A61K 39/40* (2006.01)
*C07K 16/12* (2006.01)

(52) U.S. Cl.
CPC ......... *C07K 16/125* (2013.01); *C07K 2317/22* (2013.01); *C07K 2317/569* (2013.01)

(58) Field of Classification Search
None
See application file for complete search history.

(56) References Cited

U.S. PATENT DOCUMENTS

2010/0305002 A1 12/2010 Chenchik

OTHER PUBLICATIONS

International Search Report from International Application No. PCT/RU2013/000227, filed Mar. 19, 2013, mailed Aug. 22, 2013.

Bashmakov et al, *Chlamydia trachomatis* growth inhibition and restoration of LDL-receptor level in HepG2 cells treated with mevastatin. Comparative Hepatology, 2010, 9:3.

Persson et al, Comparison of five serologic tests for diagnosis of acute infections by chlamydia pneumonia, Clinical and Diagnostic Laboratory Immunology, 2000, pp. 739-740, vol. 7, No. 5.

Cortez-Retamozo et al, Efficient cancer therapy with a nanobody-based conjugate, Cancer Research, Apr. 15, 2004, pp. 2853-2857, 64 (8).

Zhang et al, Protective monoclonal antibodies to *Chlamydia trachomatis* serovar- and serogroup-specific major outer membrane protein determinants, Infection and Immunity, Feb. 1989, pp. 636-638, vol. 57, No. 2.

Hoogenboom, Selecting and screening recombinant antibody libraries, Nature Biotechnology, Sep. 2005, pp. 1105-1116, vol. 23, No. 9.

Conrath et al, Camel single-domain antibodies as modular building units in bispecific and bivalent antibody constructs, J. Biol. Chem., Oct. 25, 2000.

Coppieters et al, Formatted anti-tumor necrosis factor alpha VHH proteins derived from camelids show superior potency and targeting to inflamed joints in a murine model of collagen-induced arthritis, Arthritis & Rheumatism, Jun. 2006, pp. 1856-1866, vol. 54 No. 6.

Harbury et al, A switch between two-, three- and four-stranded coiled coils in GCN4 leucine zipper mutants, Science, New Series, Nov. 26, 1993, pp. 1401-1407, vol. 262, No. 5138.

Vincke et al, General strategy to humanize a camelid single-domain antibody and identification of a universal humanized nanobody scaffold, The Journal of Biological Chemistry, Jan. 30, 2009, pp. 3273-3284, v. 284. No. 5.

Conrath et al, Beta-lactamase inhibitors derived from single-domain antibody fragments elicited in the Camelidae, Antimicrobial Agents and Chemotherapy, Oct. 2001, pp. 2807-2812, vol. 45, No. 10.

Saerens et al, Single domain antibodies derived from dromedary lymph node and peripheral blood lymphocytes sensing conformational variants of prostate-specific antigen, The Journal of Biological Chemistry, 2004, pp. 51965-51972, vol. 279, No. 50.

Wesolowski et al, Single domain antibodies: promising experimental and therapeutic tools in infection and immunity, Med. Microbiol. Immunol. 2009, pp. 157-174, 198.

Rothbauer et al, Targeting and tracing antigens in live cells with fluorescent nanobodies, Nature Methods, Nov. 2006, pp. 887-889, vol. 3, No. 11.

Tillib, "Camel Nanoantibody" is an efficient tool for research, diagnostics and therapy, Molecular Biology, 2011, pp. 77-85, vol. 45, No. 1.

(Continued)

*Primary Examiner* — Gary Nickol
*Assistant Examiner* — Khatol Shahnan Shah
(74) *Attorney, Agent, or Firm* — Patentbar International, P.C.

(57) ABSTRACT

A nanoantibody specifically binding surface antigen of *Chlamydia trachomatis* and having SEQ ID NO:2 amino acid sequence is disclosed. A nanoantibody specifically binding surface antigen of *Chlamydia trachomatis* and having SEQ ID NO:4 amino acid sequence is disclosed. A nanoantibody with SEQ ID NO:2 amino acid sequence inhibits development of *Chlamydia* infection caused by *C. trachomatis*. A nanoantibody with SEQ ID NO:4 amino acid sequence inhibits development of *Chlamydia* infection caused by *C. trachomatis*. A method of in vitro inhibiting a *Chlamydia* infection caused by *C. trachomatis* has the steps of pretreating elementary bodies of *C. trachomatis* by a therapeutically efficient amount of a nanoantibody specifically binding to a surface antigen of *Chlamydia trachomatis*, the nanoantibody comprising an amino acid sequence SEQ ID NO: 4 or SEQ ID NO:4, and then adding the elementary bodies of *C. trachomatis* to target cells being infected.

6 Claims, 3 Drawing Sheets

(56) References Cited

OTHER PUBLICATIONS

Tillib et al, Fingerprint-like analysis of "nanoantibody" selection by phage display using two helper phage variants, Acta Naturae, 2010, pp. 85-93, vol. 2, No. 3(6).

Hamers-Casterman et al, Naturally occurring antibodies devoid of light chains, Nature Jun. 3, 1993, pp. 446-448, vol. 363.

Sidhu et al, Phage display for engineering and analyzing protein interaction interfaces. Current Opinion in Structural Biology, 2007, 17:481-487.

Sambrook et al., Molecular cloning: a laboratory manual, 3rd ed., 2001, vol. 1, 2, 3, Cold Spring harbor Laboratory Press, Cold Spring Harbor, New York.

Muyldermans et al, Recognition of antigens by single-domain antibody fragments: the superfluous luxury of paired domains, Trends in Biochemical Sciences, Apr. 2001, vol. 26, No. 4, pp. 230-235.

Deyev et al, Design of multivalent complexes using the barnase*barstar module, Nature Biotechnology, Dec. 2003, vol. 21, No. 12, pp. 1486-1492.

Nguyen et al, Functional heavy-chain antibodies in Camelidae, Advances in Immunology, 2001, vol. 79, pp. 261-296.

Zhang et al, Pentamerization of single-domain antibodies from phage libraries: a novel strategy for the rapid generation of high-avidity antibody reagents, J Mol. Biol. 2004, vol. 335, pp. 49-56.

Padlan E. A., X-Ray crystallography of antibodies, Advances in Protein Chemistry, 1996, vol. 49, pp. 57-133.

Shiraishi et al, Increased cytotoxicity of soluble Fas ligand by fusing isoleucine zipper motif, Biochemical and Biophysical Research Communications, 2004, pp. 197-202, vol. 322.

Brissette et al, The use of phage display peptide libraries for basic and translational research, Methods in Molecular Biology, 2007, pp. 203-213, vol. 383: Cancer Genomics and Proteomics: Methods and protocols, Humana Press, Inc., Totowa, NJ.

Baral et al, Experimental therapy of African trypanosomiasis with a nanobody-conjugated human trypanolytic factor, Nature Medicine, May 2006; pp. 580-584, vol. 12 No. 5.

SEQUENCE LISTING

<160> NUMBER OF SEQ ID NOS: 4

<210> SEQ ID NO 1
<211> LENGTH: 378
<212> TYPE: DNA
<213> ORGANISM: CHLAMYDIA TRACHOMATIS

<400> SEQUENCE: 1
atggccctgc aggtgcagct ggtggagtct gggggaggct cggtgcaggc tggagggtct 60
ctgagactct cctgtacgac ctctcactac gtcgccagta actcctgcat ggcctggttc 120
cgccaggctc cggggaaaaa gcgcgagggg gtcgcaagta tcagccgtcg tgctgatatc 180
acattctatg ccgactccgt gaaggaacga ttcgtcatct cacgcgacaa ttccgagcgc 240
acgctgtatc tacaaatgaa cagcctgaaa cctgaggaca ctgccatgta ctactgtgcg 300
gcagatctca gctactgcgg gttgaccgag gagggctata atcactgggg ccaggggacc 360
caggtcaccg tctcctca 378

<210> SEQ ID NO 2
<211> LENGTH: 126
<212> TYPE: PRT
<213> ORGANISM: CHLAMYDIA TRACHOMATIS

<400> SEQUENCE: 2

Met Ala Leu Gln Val Gln Leu Val Glu Ser Gly Gly Gly Ser Val Gln
1 5 10 15

Ala Gly Gly Ser Leu Arg Leu Ser Cys Thr Thr Ser His Tyr Val Ala
20 25 30

Ser Asn Ser Cys Met Ala Trp Phe Arg Gln Ala Pro Gly Lys Lys Arg
35 40 45

Glu Gly Val Ala Ser Ile Ser Arg Arg Ala Asp Ile Thr Phe Tyr Ala
50 55 60

Asp Ser Val Lys Glu Arg Phe Val Ile Ser Arg Asp Asn Ser Glu Arg
65 70 75 80

Thr Leu Tyr Leu Gln Met Asn Ser Leu Lys Pro Glu Asp Thr Ala Met
85 90 95

Tyr Tyr Cys Ala Ala Asp Leu Ser Tyr Cys Gly Leu Thr Glu Glu Gly
100 105 110

Tyr Asn His Trp Gly Gln Gly Thr Gln Val Thr Val Ser Ser
115 120 125

-continued

```
<210> SEQ ID NO 3
<211> LENGTH: 396
<212> TYPE: DNA
<213> ORGANISM: CHLAMYDIA TRACHOMATIS

<400> SEQUENCE: 3

atggccctgc aggtgcagct ggtggagtct gggggaggat cggtgcaggc tggaggctcc     60

ctgagactgc actgtgcatc ctctggatat gttgaagcta ggatcttgat gggctggttc    120

cgccaggctc ccgggaagga gcgcgagggg gtcgcggcca tttatattgg tgatggtact    180

acagattatg gcgactccgt gaagggccgg ttcaccgtct ctcaagacgg cgccaagaac    240

gcgatctatc tgcacatgta cgacgtgaaa cctgaggacg ctgccacata ctactgtgcg    300

gcaggtatta tgccttggta tcgaacgtgg agcggaagac tcaacgtggg tgactttgat    360

tcgtggggcc aggggaccca ggtcaccgtc tcctca                              396


<210> SEQ ID NO 4
<211> LENGTH: 132
<212> TYPE: PRT
<213> ORGANISM: CHLAMYDIA TRACHOMATIS

<400> SEQUENCE: 4

Met Ala Leu Gln Val Gln Leu Val Glu Ser Gly Gly Gly Ser Val Gln
1               5                   10                  15

Ala Gly Gly Ser Leu Arg Leu His Cys Ala Ser Ser Gly Tyr Val Glu
            20                  25                  30

Ala Arg Ile Leu Met Gly Trp Phe Arg Gln Ala Pro Gly Lys Glu Arg
        35                  40                  45

Glu Gly Val Ala Ala Ile Tyr Ile Gly Asp Gly Thr Thr Asp Tyr Gly
    50                  55                  60

Asp Ser Val Lys Gly Arg Phe Thr Val Ser Gln Asp Gly Ala Lys Asn
65                  70                  75                  80

Ala Ile Tyr Leu His Met Tyr Asp Val Lys Pro Glu Asp Ala Ala Thr
                85                  90                  95

Tyr Tyr Cys Ala Ala Gly Ile Met Pro Trp Tyr Arg Thr Trp Ser Gly
            100                 105                 110

Arg Leu Asn Val Gly Asp Phe Asp Ser Trp Gly Gln Gly Thr Gln Val
        115                 120                 125

Thr Val Ser Ser
    130
```

NANOANTIBODIES, BINDING *CHLAMYDIA TRACHOMATIS* ANTIGEN, METHOD FOR INHIBITION OF INFECTION INDUCED BY *CHLAMYDIA TRACHOMATIS*

RELATED APPLICATIONS

This application is a Continuation application of International Application PCT/RU2013/000227, filed on Mar. 19, 2013, which in turn claims priority to Russian Patent Applications No. RU 2012101955, filed Jan. 20, 2012, both of which are incorporated herein by reference in their entirety.

FIELD OF THE INVENTION

The invention refers to biotechnology and medicine, especially to isolation and use of single domain nanoantibodies for detection and suppression of infection induced by pathogenic microorganisms, especially, *Chlamydia trachomatis.*

BACKGROUND OF THE INVENTION

*C. trachomatis* is a gram-negative bacterium that refers to an obligate intracellular human pathogen. *Chlamydia* has two-phase cycle of development that consists of two forms of pathogen existence: extracellular elementary bodies and intracellular reticular bodies.

One of the most common bacterial STD in men and women is an urogenital infection (UGI) caused by *C. trachomatis.*

There are over 20 nosological forms among diseases induced by *C. trachomatis* species where special role plays sexually transmitted urogenital *Chlamydia* infection (UGCI) affecting human urogenital tract. Urogenital *Chlamydia* infection—cervicitis, urethritis, proctitis, endometritis, salpingitis, perihepatitis—in women; urethritis, epididymitis, proctitis, prostatitis—in men—are most common among sexually active population.

*Chlamydia* are detected in 50-57% of sterility cases. There are observed not only functional disorders of reproduction, but also involvement of homeostasis control systems, immune competent cells etc. *Chlamydia* infections incidence in case of tubal infertility is from 41 to 54%. After first case of chlamydiosis the risk of tubal infertility increases by 10%, after third case—by 50%. In infertile couples 50-55% of men are sterile, and in 64% of these cases sterility is caused by UGCI. *Chlamydia* can cause infertility as a result of direct exposure on sperm due to tight adhesion of *Chlamydia* on male gametes that prevents impregnating the ovum. Some authors note that secondary female infertility in case of ascending UGCI is observed more often (in 6 times) than in case of gonorrhea.

*C. trachomatis* is observed in 9-30% of cases of ectopic pregnancy. In recent years has been noted increase of chlamydiosis of pregnant (10-40%) and newborns. In 40-60% of cases infected women transmit infection to newborns.

UGI's are diagnosed in 46% of cases at the age of 15-19 years old, and in 30% at the age of 20-24 years old. Incidence is quite high not only among adult population and teenagers having sexual relations but also among younger children without sexual relations. Thus, *C. trachomatis* has been observed in 67.4% of boys under 12 years old with UGI. In this case clinical picture of UGCI conformed to urethritis, and ultrasonography showed traces of past prostatitis in 7.9% of children.

It is very important that 75% of women and 40% of men had asymptomatic disease, and 30-40% of teenagers had latent *Chlamydia* infection proceeding from 2 to 5 years. Asymptomatic disease is typical not only for Urogenital localization, but also for infections of other organs. Epidemiological importance of asymptomatic *Chlamydia* infection was shown in works of A. Shatkin, the founder of Chlamydiology in Russia. *Chlamydia* isn't a member of normal human flora. Detection of it indicates infectious process, and the absence of clinical symptoms determines only temporary balance between a parasite and a host under conditions limiting but not inhibiting growth of intracellular pathogens. In this regard, *Chlamydia* infection with clinical asymptomatic course is dangerous as its manifest forms and needs treatment and prevention. Undiagnosed, untreated or improperly treated patients with acute, subacute or slow *Chlamydia* inflammatory processes are most attributable to incidence of infection nowadays.

In many developed countries of Europe and the US national UGCI control programs based on screening of high-risk population, early treatment, examination and treatment of partners have been realized for over 25 years. Despite these actions, cases of primary chlamydiosis and reinfection have still increased.

During recent years incidence of urogenital *Chlamydia* infections in the Russian Federation has come out on top among all the sexually transmitted bacterial infections and it gives way only to trichomoniasis.

According to Central Scientific and Research Institute for Organization and Information Support of Health Care FSU, UGCI incidence comparing to 1994 increased in 1.7 times (61.4 versus 101.7). In 2005, total number of STD cases amounted to 503.6 per 100000 of population, in 2006—decreased to 4.1%. However, UGCI in 2005 amounted to 95.9 per 100000 (adults) and 3.1 per 100000 (children); in 2006—97.2 per 100000; in 2007—91.1 per 100000 (adults) and 3.2 per 100000 (children).

In 2008, 611634 cases of sexually transmitted infections were registered, that amounted to 403.5 per 100000 of population. *Chlamydia* infection amounted to 20.8%. For the last 3 years reduction of patients with STD (including 8.4% with *chlamydia* infection) is observed all over the Russia. Incidence of *Chlamydia* infection in Russia in 2008 was 89.5 per 1000000 of adult population and 2.8 per 100000 of children.

So medical and social role of *Chlamydia* infection is firstly caused by high incidence and frequent complications, and also by effect on demographic determinants due to fact that UGCI is the most frequent cause of female and male infertility.

Urogenital chlamydiosis therapy represents the most difficult aspect of the concerned issue, which is associated not only with features of infectious agent and its development cycle but also with association of chlamydiosis with other infection in 70% of cases: ureaplasma, herpes simplex virus, *Gardnerella vaginalis* etc. Causal treatment is based on chlamydial antibiotics susceptibility. Widespread use of tetracycline antibiotics in treatment of chlamydiosis (doxycycline, metacycline, minocycline, and tetracycline) is quite reasonable. According to WHO recommendations: 100 mg doxycycline orally twice a day or 500 mg tetracycline orally 4 times a day, course of treatment—7 days. It must be noted that number of ineffective treatment cases has significantly increased recently, which, probably, may be due to resistance of causative agent to antibiotic in population. Doses and treatment duration must be adjusted evidently depending on UGCI course (acute, chronic, ascending infection, exacerbation etc.). The most conflicts of researchers are related to use of fluroquinolone antibiotics: ofloxacin, pefloxacin, ciprofloxacin. Some authors report efficient ofloxacin therapy in 81-100% of cases (200-300 mg per os twice a day during 7 days); others report high failure rate and the worst long-term outcomes. Treatment of chronic, complicated forms of chlamydiosis currently presents very serious and unresolved problem. This is firstly related to fact that during chronization of infectious process in macroorganism occur persisting forms of *Chlamydia* that are antibiotic-resistant and are adjusted to long term survival. That is why treatment of chronic forms of UGCI with antibiotics, according to numerous clinical and microbiological studies, is inefficient. The situation makes development of new antibacterial products, mechanism of action of which shall be fundamentally different comparing to antibiotic action, very important.

Murine monoclonal antibodies specific to major outer membrane protein (MOMP) of *C. trachomatis*, can act as the closest technical decision analog, making the ground of the present invention. Antibodies were prepared by standard method of isolation of monoclonal antibodies based on hybridome technology with mice immunization. Isolated antibodies recognized MOMP of *C. trachomatis*, identifying epitopes, localized at the surface of *Chlamydia* cell. Antibodies reduced toxicity of causative agent in mice in vivo.

Zhang, Y.-X., S. J. Stewart, and H. D. Caldwell. Protective monoclonal antibodies to *Chlamydia trachomatis* serovar- and serogroup-specific major outer membrane protein determinants. Infect. Immun. 1989, 57:636-638 (SUPPLEMENT 1)

This technical decision as the closest to the claimed one regarding active ingredient composition and mode of its use has been chosen by the authors of this invention as a prototype.

The disadvantages of the prototype are:

1) Relatively expensive production of antibodies, difficulties in maintaining and storage of the producer, extremely high requirements to quality of the used reagents and culture conditions.

2) Relatively large size of isolated antibodies resulting in low tissue permeability.

3) Structural characteristics impose restrictions on recognition of some "hidden" epitopes located, in clefts, fissures of small size in protein structures.

4) Limitation and relative complexity of genetic engineering manipulations, adaptations for specific issues, difficulties in creation of multivalent and multifunctional derivatives of specified antibodies.

Thus, there is a need in development of new antibodies—antigen-recognizing molecules without any of the said disadvantages and specifically recognizing *C. trachomatis*, in the technical level.

SUMMARY OF THE INVENTION

The object of present invention is a creation of new antibodies, able to effectively recognize antigens of *C. trachomatis* and inhibit chlamydial infection. Its isolation, production and storage must be cost-effective, efficient and about simple. It must be much smaller than classical antibodies.

Assigned problem is solved by construction of nanoantibody (with SEQ ID NO:2 amino acid sequence) specifically binding to surface *Chlamydia trachomatis* antigen. Nanoantibody, specifically binding surface antigen of *Chlamydia trachomatis*, with SEQ ID NO:4 amino acid sequence has also been constructed. Nanoantibody with SEQ ID NO:2 amino acid sequence inhibits development of *Chlamydia* infection induced by *C. trachomatis*. Nanoantibody with SEQ ID NO:4 amino acid sequence inhibits development of *Chlamydia* infection induced by *C. trachomatis*. Method of inhibition of *Chlamydia* infection in vitro, induced by *C. trachomatis*, involving pretreatment of elementary bodies of *C. trachomatis* by therapeutically efficient volume of nanoantibody with SEQ ID NO:2 amino acid sequence before adding it to target cell, has been claimed. Method of inhibition of *Chlamydia* infection in vitro, induced by *C. trachomatis*, involving pretreatment of elementary bodies of *C. trachomatis* by therapeutically efficient volume of nanoantibody with SEQ ID NO:4 amino acid sequence before adding it to target cell, has been claimed.

The basis of the invention are not classical bivalent antibodies, considered as a prototype, but small nanoantibodies with variety of advantages comparing to classical monoclonal antibodies for practical use in the sphere of disease therapy. As long as nanoantibodies with molecular mass of about 12-15 kDa are 10 times smaller than the size of traditional antibodies, they get numerous positive features of practical importance. There are efficient ways of isolation and selection of such antibodies specific to various antigens and, due to their low immunogenicity, nanoantibodies may be used for treatment of infections induced by pathogens of this family.

Absolute equivalent of the term "nanoantibodies" for the purposes of the present invention is a widely used denomination "NANOBODY", introduced by ABLYNX, and also "single-domain mini-antibody" and "single-domain nanoantibody".

Recombinant nanoantibodies production is based on specific nonclassic single-chain antibodies, existing naturally together with classic antibodies in Camelids (and some species of cartilaginous fishes). These specific antibodies consist of dimer of only one short (without first constant CH1 region) heavy immunoglobulin chain and are fully functional in the absence of the light immunoglobulin chain. Only one variable domain (VHH, "nanoantibody", "nanobody" or single-domain nanoantibody) of this antibody is necessary and sufficient for specific recognition and binding of antigen. Organization of variable domains (VHH) of nonclassic antibodies is largely similar to that of the variable domains (VH) of classic antibodies (human VH-domains of subclass IgG3 immunoglobulins have most evident homology with VH and VHH of Camelids). In both cases V-domains consist of four conservative framework regions (FR), surrounding three hypervariable complementarity determining regions CDR. In both cases domains form typical for immunoglobulin V-domain spatial structure of two beta-layers: the first—from four amino acid chains, and the second—from five [Padlan E. A. X-Ray crystallography of antibodies. Adv. Protein Chem. 1996; 49: 57-133. Muyldermans S., Cambillau C., Wyns L. Recognition of antigens by single-domain antibody fragments: the superfluous luxury of paired domains. TIBS 2001; 26: 230-235]. In this structure all of three hypervariable regions cluster at one side of V-domain (where they take part in recognition of antigen) and are located in loops binding beta-structures. However, there are also significant distinctions, attributed to VHH functioning in the single domain format. Thus, hypervariable CDR1 and CDR3 regions are visibly increased in case of VHH. Cysteine residues are often detected in hypervariable VHH regions being present in two regions at one time (the most often in CDR1 and CDR3, less often—in CDR2 and CDR3). It was shown that these cysteine residues formed disulfide bonds that leaded to additional stabilization of the present antigen loop structure in crystal structures analysis of VHH. The most obvious and reproductive distinctive feature of VHH are four changes of hydrophobic amino acid residues to hydrophilic in the second framework region (Val37Phe, Gly44Glu, Leu45Arg, Trp47Gly, according to Kabat Numbering Scheme). This framework region in case of VH domain is highly conserved, enriched with hydrophobic amino acid residues, and is critical for bonding with VL variable domain of the light chain. VHH-domain is quite different in this context: the designated changes of hydrophobic amino acids to hydrophilic let to impossibility of VHH and VL association. Such changes also explain high solubility of VHH, nanoantibody, when it is isolated in the form of recombinant protein [Tillib S. V. "camel antibodies"—effective instrument for studies, diagnostics and therapy. Molecular biology 2011; 45(1): 77-85].

Camel nanoantibodies have variety of advantages which allows to assume great potential for their future use in various studies and in creating new biotechnological devices, and also for clinical purposes in diagnostics and treatment of diseases compared to traditional and purely recombinant antibodies.

Unique features of nanoantibodies determining great potential of their use for variety of practical applications in immune biotechnology are [See overview: Tillib S. V. "camel antibodies"—effective instrument for studies, diagnostics and therapy. Molecular biology 2011; 45(1): 77-85];

1) Highly efficient method of generating and selection of nanoantibodies.

2) Small size, ~2×4 nm, 13-15 kDa, enhanced cell permeability.

3) Structural properties, i.e. ability to form unusual for classical antibodies paratopes, allowing to bind with clefts and binding sites of proteins; can be used for detection of "hidden" epitopes that cannot be recognized by ordinary antibodies.

4) High expression rate, cost efficient development in large volume. Nanoantibodies are usually developed in *E. coli* periplasm (amounting to 1-10 mg of 1 L of culture). Possible development in yeast, plants and cells of mammals.

5) Simplicity of all the possible genetic engineering manipulations, adaptations for specific issues, possibility to create multivalent and multifunctional derivatives.

6) Low immunogenicity; possibility to economically "humanize" antibodies without significant loss of their specific activity.

Possibility to isolate recombinant nanoantibodies with given specificity is determined by functional nonclassic antibodies with quite wide recognition spectrum intrinsic to representatives of Camelidae family. Nonclassic antibodies consist of dimer of only one short heavy immunoglobulin chain without light chains, recognition specificity of which is determined by only one variable domain [Hamers-Casterman C, Atarhouch T, Muyldermans S, et al. Naturally occurring antibodies devoid of light chains. Nature 1993; 363:446-448]. Technical realization of selection of nanoantibodies (that are genetically engineered derivatives of antigen-recognizing domains of single chain camel antibodies) is based on high-efficient selection procedure of antigen-recognizing polypeptides, exposed on the surface of the filamentous phage particle—"phage display".

Phage display method is quite efficient and widely used technique for functional selection of DNA sequences from large recombinant libraries, encoding peptides and proteins, having given properties and expressed on the surface protein composition of filamentous phages [Brissette R & Goldstein N I. The use of phage display peptide libraries for basic and translational research. Methods Mol Biol. 2007; 383:203-13; Sidhu S S & Koide S. Phage display for engineering and analyzing protein interaction interfaces. Curr Opin Struct Biol. 2007; 17:481-7]. One of the most important applications of this technique is generation of specific recombinant antibodies for different antigens [Hoogenboom H R. Selecting and screening recombinant antibody libraries. Nat Biotechnol. 2005; 23:1105-16]. Normally hybrid recombinant single-chain proteins are used instead of large whole molecules of classic antibodies for exposure at the phage surface. These hybrid recombinant single-chain proteins have random combinations of cloned sequences in variable regions of heavy and light immunoglobulin chains bound with short serine/glycine-enriched linker sequence. Such chimeric molecule in case of right domain combination can keep specificity of initial immunoglobulin, despite of the implemented changes compared to native antibodies molecule. One of the problem in traditional recombinant technologies is need to work with extremely large libraries of recombinant antibodies, where all possible combinations of two random variable regions (heavy and light chains of immunoglobulins) bound by linker sequence must be represented. There is also another problem apart from the representation issue. This problem consists of formation of the right relative conformation of these two domains and also of solubility of individual variable domains very often tending to adhesion. These issues can be avoided using nanoantibodies, as long as virtually every cloned variable domain of single-chain antibodies shall in this case possess a certain antigen-recognizing specificity, corresponding to one of the antibodies of immunized animal, and selection can be effectively performed from relatively small libraries of such domains.

Nanoantibodies with certain specificity or their derivatives can be used, as can classical antibodies, in various applications, including, but not limited to, antigen detection both for research and diagnostic purposes, suppression of protein-antigen activity, specific delivery by binding to antigen of desired molecules, conjugated with antibody. Nanoantibodies can also be initial modules-units of more complicated multimodule products. Unification in one multivalent derivative of two, three and more monovalent primary nanoantibodies is possible. These nanoantibodies unified into one construct can be bound to the same epitope of target antigen, and its different epitopes, or even to various target antigens. Combined unification into one construct of nanoantibodies and other molecules or products for obtainment of multifunctional products is also possible [Conrath K E, Lauwereys M, Wyns L, Muyldermans S. Camel single-domain antibodies as modular building units in bispecific and bivalent antibody constructs. J Biol Chem. 2001 Mar. 9; 276 (10): 7346-50; Zhang J, Tanha J, Hirama T, Khieu N H, To R, Tong-Sevinc H, Stone E, Brisson J R, MacKenzie C R. Pentamerization of single-domain antibodies from phage libraries: a novel strategy for the rapid generation of high-avidity antibody reagents. J Mol Biol. 2004 Jan. 2; 335 (1): 49-56; Cortez-Retamozo V, Backmann N, Senter P D, Wernery U, De Baetselier P, Muyldermans S, Revets H. Efficient cancer therapy with a nanobody-based conjugate Cancer Res. 2004 Apr. 15; 64 (8): 2853-7; Baral T N, Magez S, Stijlemans B, Conrath K, Vanhollebeke B, Pays E, Muyldermans S, De Baetselier P. Experimental therapy of African trypanosomiasis with a nanobody-conjugated human trypanolytic factor. Nat. Med. 2006 May; 12 (5): 580-4; Coppieters K, Dreier T, Silence K, Haard H D, Lauwereys M, Casteels P, Beirnaert E, Jonckheere H, Wiele C V, Staelens L, Hostens J, Revets H, Remaut E, Elewaut D, Rottiers P. Formatted anti-tumor necrosis factor alpha VHH proteins derived from camelids show superior potency and targeting to inflamed joints in a murine model of collagen-induced arthritis. Arthritis Rheum. 2006 June; 54 (6): 1856-66]; multimerization by introduction of additional amino acids sequences of interacting protein domains, such as leucine zippers [Harbury P. B., Zhang T., Kim P. S., et al. A switch between two-, three- and four-stranded coiled coils in GCN4 leucine zipper mutants. Science, 1993, 262:1401-1407; Shirashi T., Suzuyama k., Okamoto H. et al. Increased cytotoxicity of soluble Fas ligand by fusing isoleucine zipper motif. Biochem. Biophys. Res. Communic. 2004, 322: 197-202; Chenchik A., Gudkov A., Komarov A., Natarajan V. Reagents and methods for producing bioactive secreted peptides. 2010. US Patent Application 20100305002], or small proteins sequences, making stable complexes [Deyev S M, Waibel R, Lebedenko E N, Schubiger A P, Plückthun A. Design of multivalent complexes using the barnase*barstar module. Nat Biotechnol. 2003, 21(12): 1486-92.].

It has also been shown [Vincke C., Loris R., Saerens D., et al.//J. Biol. Chem. 2009. V. 284. No. 5. P. 3273-3284], that these camel nanoantibodies can be "humanized" without evident loss of their specific activity, making little number of point amino acid replacements. This gives potential to wide usage of nanoantibodies for passive immunization to prevent development of various infectious diseases [Wesolowski J., Alzogaray V., Reyelt J. et al. Single domain antibodies: promising experimental and therapeutic tools in infection and immunity. Med. Microbiol. Immunol. 2009; 198, 157-174.].

Method for isolation of nanoantibodies binding antigens of *C. trachomatis* is performed based on selection by phage display method, genetic engineering modifications encoding sequences of these antibodies and using them as an active ingredient producer (antibody) of *E. coli*. Nanoantibodies (molecular weight about 12-15 kDa) are 10 times smaller than the size of traditional classical antibodies and are fully functional antigen-recognizing units, possessing numerous positive features of practical importance. Nanoantibody is a easily soluble single-domain protein with high stability (in a wide range of temperatures and pH). This helps to avoid problems with solubility and right folding of antibodies molecules during production by prokaryotic cells and leads to significant reduction of production costs comparing to traditional methods of therapeutic monoclonal antibodies isolation in eukaryotic expression systems. Process of preservation and transport of antibodies is significantly simplified comparing to evidently less stable traditional antibodies. Due to their little size nanoantibodies are characterized by better ability to penetrate in tissues. Finally, nanoantibodies facilitate genetic engineering manipulations with the purpose of subsequent production of bispecific nanoantibodies or chimeras, consisting of the second protein with desired properties apart from nanoantibody.

Despite the fact that authors used production of antibodies using *E. coli* for illustration of this invention, it is obvious for an average skilled specialist in this art that the volume of the present invention also involves other variants of realization systems for this invention, not specifically stated herein. For example, yeast cultures or other systems standard for this art may be used as eukaryotic producer.

The method for isolation of nanoantibodies has been described in examples 1 and 2. Choosing realization methods, with the purpose of isolation of nanoantibodies with the selected properties from prokaryotic expression system in accordance with one of the desired options for performance of this invention, is conditioned upon the following factors:

1) High expression rate, cost efficient development in large volume, provided by nanoantibodies expression in *E. coli* periplasm amounting to 1-10 mg of 1 L of culture.

2) Simplicity of all possible genetic engineering manipulations, adaptations for specific issues, possibility to create multivalent and multifunctional derivatives.

3) High economic efficiency of production.

The authors of this invention assumed that, as the average skilled specialist in this art knows, primary, initial sequences of nanoantibodies can be later adjusted or "formated" in various ways for subsequent practical use. Thus, nanoantibodies can be initial modules-units of more complicated multimodule products. Unification in one multivalent derivative of two, three and more monovalent primary nanoantibodies is possible. These nanoantibodies unified into one construct can bind both with the same epitope of target antigen, and its different epitopes, or even with various target antigens. Combined unification into one construct of nanoantibodies and other molecules or drugs with isolation of multifunctional preparations, multimerization by means of introduction of new additional amino acid sequences, interactive protein domains such as leucine zippers or small proteins sequences, forming stable complexes, are possible. For modulation of properties of nanoantibody products (e.g. life time increment or purification method enhancement) additional amino acid sequences may be introduced into content of the end compound. It will be evident for an average specialist of this art that such modifications and other variants of antibodies, underlying in this invention, are involved into volume of this invention, because they are structural and functional variants of nanoantibodies. In this wise, under the term "nanoantibodies" authors of this invention mean both primary, initial "minimal" amino acid sequences of nanoantibodies, and their modifications obtained as a result of the designated adaptations or "formatting" and their variants. The term "antibody variant" for the purpose of this invention means polypeptide with changes in amino acid sequence, i.e. deletion, insertion, addition or substitution of amino acids, provided that the needed protein activity level is preserved, for instance, at least 10% of activity of the initial nanoantibody. Several changes in protein variant depend on location or type of amino acid residue in 3D protein structure. Number of changes may amount, for example, from 1 to 30, more preferably from 1 to 15, and the most preferably from 1 to 5 changes in initial nanoantibody sequence. These changes can take place in regions of polypeptide that are not critical for its function. This can be possible owing to that fact, that some amino acids possess high homology with each other and that is why tertiary structure or protein activity are not violated in this change. That is why protein characterized by homology not less than 70%, preferably, not less than 80%, more preferably, not less than 90%, and the most preferably, not less than 95% regarding amino acid sequence of initial nanoantibody can be an option, provided that polypeptide activity is preserved. Homology between amino acid sequences can be established using well known methods, for example, sequence alignment in BLAST 2.0 computer application, calculating three parameters: count, identity and similarity.

Deletion, insertion, addition or substitution of one or several amino acid residues shall represent conservative mutation or conservative mutations, provided that in this case protein activity is preserved. Conservative substitution is an example of conservative mutation (s). "Conservative amino acid substitution" is a substitution when amino acid residue is replaced by amino acid residue, having similar side chain. In this art amino acid families with similar side chains are determined. These families include amino acids with main side chains (for example, lysine, arginine, histidine), acidic side chains (for example, aspartic acid, glutamic acid), chargeless polar side chains (for example, glycine, asparagine, glutamine, serine, threonine, tyrosine, cysteine), nonpolar side chains (for example, alanine, valine, leucine, isoleucine, proline, phenylalanine, methionine, tryptophan), beta-branched side chains (for example, threonine, valine, isoleucine) and aromatic side chains (for example, tyrosine, phenylalanine, tryptophan, histidine). As far as hypervariable regions of nanoantibodies determine their specific interaction with antigen, that is why homological amino acid substitutions in these regions exactly may lead to isolation of several sequence-varied nanoantibodies, having identical or similar properties. So an average skilled specialist of this art shall obviously understand that the volume of this invention shall involve not only specified in the supplement nanoantibodies sequences, but also those that can be isolated by amino acid substitutions in hypervariable regions, listed in the sequences list as CDR to others, but with very similar properties, amino acids of conservative substitutions.

DNA fragments, that are virtually encoding the same functional polypeptide, can be isolated, for example, by modification of DNA fragment nucleotide sequence, encoding initial nanoantibody, for example, by site-directed mutagenesis method, so that one or several amino acid residues in the specific site will be deleted, substituted, inserted or added. DNA fragments, modified as described above, can be isolated by traditional treatment methods for mutation.

DNA fragments, virtually encoding the same functional polypeptide of the initial nanoantibody, can be isolated by expression of DNA fragments with above mutation, and establishment of activity of the expressed product.

Substitution, deletion, insertion or addition of the above nucleotides also involve mutations occurring in nature and, for example, can be attributed to variability.

Polypeptides of nanoantibodies considered in this invention can be encoded by numerous molecules of nucleic acids, which is a result of famous in this art phenomenon of code degeneracy. The essence of phenomenon consists in that fact that any amino acid (excluding tryptophan and methionine) in the composition of natural peptides, can be encoded by more than one triplet nucleotide codon. Any of these degenerated encoding molecules of nucleic acids can be a part of cassettes, expressing antibodies stated in accordance with this invention and involved into the volume of this invention.

Isolation of functional active nanoantibodies, recognizing antigens of *C. trachomatis* is illustrated in examples 3, 4.

Inhibiting effect of therapeutically efficient number of nanoantibodies on the development of *Chlamydia* infection is illustrated in example 5.

B—photomicrography of MIF results with aCt2 (10 μ/ml)

1—*C. trachomatis,* 2—ovalbumin protein, 3—*C. pneumoniae,* 4—C. muridarum, 5—*C. psittaci.*

Figure 2:
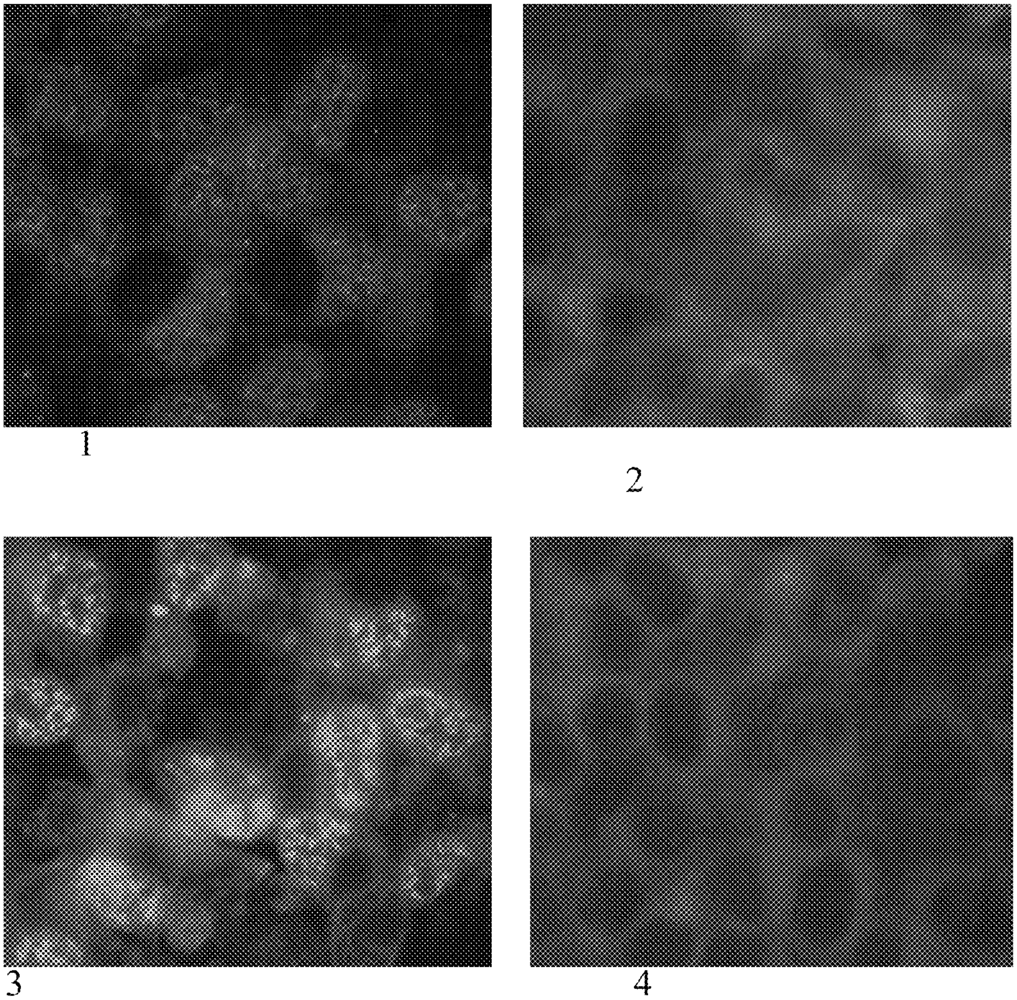
Figure 3:
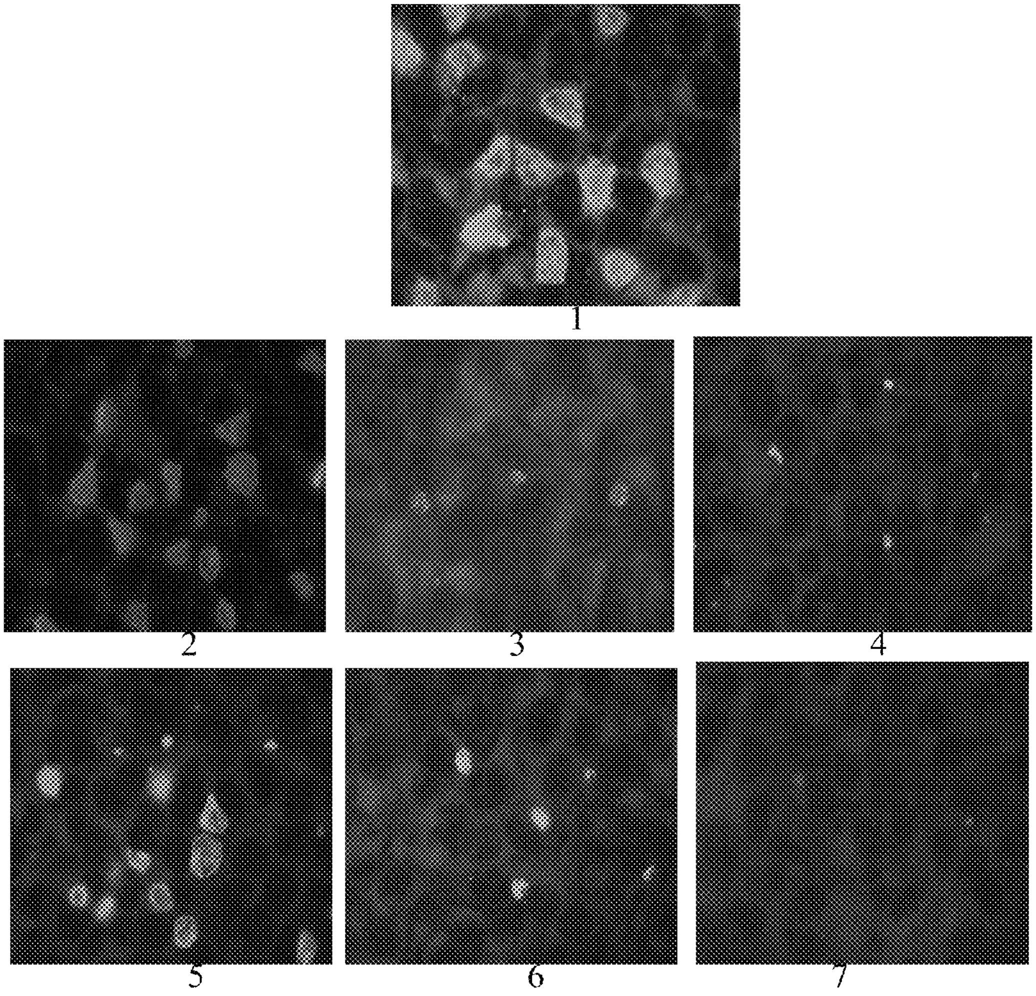

FIG. 2 represents results of analysis for specific binding of single domain nanoantibodies specifically with *C. trachomatis*, forming intracellular inclusions in eukaryotic cells, where 1—McCoy cells, infected with *C. trachomatis* and dyed with aCt1, 2—nanoantibodies—noninfected McCoy cells dyed with aCt1 nanoantibodies 3—McCoy cells, infected with *C. trachomatis* and dyed with aCt2 nanoantibodies 4—noninfected McCoy cells dyed with aCt2 nanoantibodies FIG. 3 illustrates results of inhibiting effect analysis of aCt1 and aCt2 nanoanibodies on *C. trachomatis* in vitro in neutralization reaction of intracellular forms—elementary bodies of *Chlamydia.*

1—McCoy cells 48 hours after infection with *C. trachomatis* (control)

2—McCoy cells 48 hours after infection with *C. trachomatis*, preincubated with 1 μg/ml aCt1

3—McCoy cells 48 hours after infection with *C. trachomatis*, preincubated with 5 μg/ml aCt1

4—McCoy cells 48 hours after infection with *C. trachomatis*, preincubated with 10 μg/ml aCt1

5—McCoy cells 48 hours after infection with *C. trachomatis*, preincubated with 1 μg/ml aCt2

6—McCoy cells 48 hours after infection with *C. trachomatis*, preincubated with 5 μg/ml aCt2

7—McCoy cells 48 hours after infection with *C. trachomatis*, preincubated with 10 μg/ml aCt2.

DETAILED DESCRIPTION OF THE INVENTION

Further are represented nucleic and amino acid sequences of two selected nanoantibodies, aCt1 and aCt2, isolated concurrently by the same method and having the desired properties: ability to specifically bind *Chlamydia trachomatis*. Nucleic cDNA sequences encoding two selected nanoantibodies have been determined for aCt1—SEQ ID NO: 1; for aCt2—SEQ ID NO: 3, the relevant amino acid sequences of selected nanoantibodies have been selected out of them: for aCt1—SEQ ID NO: 2; for aCt2—SEQ ID NO: 4. Hypervariable regions of antigen recognizing sequences of selected nanoantibodies from left to right, from N- to C-end CDR1, CDR2 and CDR3 have been underlined in the designated sequences. The arrows show positions of amino acid residues that are characteristic for variable domains of specific single chain antibodies differing from residues in variable domains of heavy chains in classical antibodies.

EXPERIMENTAL

Example 1

Isolation of library of variable domains in single chain antibodies

Immunization.

*Camelus bactrianus* had been consistently immunized for 5 times by subcutaneous injection of antigenic material, mixed with equal portion of incomplete Freund's adjuvant. The product of native purified elementary particles of Bu-434 *C. trachomatis* strain (whole bacterial cells), inactivated by UV-irradiation, and protein complex product of the outer membrane of cell wall of Bu-434 *C. trachomatis* strain without LPS was used as an antigen. The second immunization was performed in 3 weeks after the first one, followed by two more immunizations in two week interval. Blood (150 ml) was sampled 6 days after the last injection. To prevent from coagulation of the sampled blood 50 ml of standard phosphate buffer solution (PBS), containing heparin (100 un/ml) and EDTA (3 mM) has been added.

The blood has been twice diluted in PBS containing 1 mM EDTA. 35 ml of diluted blood solution was coated on surface of special medium (Histopaque-1077, Sigma) with density 1.077 g/ml and volume of 15 ml and then was centrifuged for 20 mM at 800 g. Mononuclear cells (lymphocytes and monocytes) were sampled from interphase zone plasma/Histopaque, followed by washing with PBS, containing 1 mM EDTA.

Total RNA from B-lymphocytes was isolated using TRIzol (Invitrogen) reagent. Later at the column with oligo (dT)-cellulose poly(A)containing RNA has been purified from total RNA. RNA concentration has been determined using Biophotometer (Eppendorf) and the quality of isolated RNA was verified by electrophoresis in 1.5% agarose gel with formaldehyde.

Reverse transcription reaction was performed according to standard protocol [Sambrook et al., 1989] using reverse transcriptase H-M-MuLV and oligo(dT)15primer.

Reverse transcriptase products were used as a matrix in two stage polymerase chain reaction and the isolated amplification products were cloned at sites NcoI(PstI) and NotI into phagemid vector, as described above [Hamers-Casterman et al., 1993; Nguyen et al., 2001; Saerens et al., 2004; Rothbauer et al., 2006]. Selection was performed similarly to those in specified works. It was based on phage display method, where bacteriophage M13KO7 (New England Biolabs, USA) is used as a helper phage.

Example 2

Selection of nanoantibodies specifically recognizing *C. trachomatis.*

Nanoantibodies were selected by phage display method using 2 products: purified elementary bodies *C. trachomatis* Bu-434 and protein complex of cell wall outer membrane of Bu-434 *C. trachomatis* strain without LPS immobilized at the bottom of wells of 96-well reaction plate. High sorption polystyrene immunological plates MICROLON 600 (Greiner Bio-One) were used. One percent BSA (Sigma-Aldrich, USA) and/or 1% nonfat milk (Bio-Rad, USA) in PBS were used as blocking buffer. Process of selection and subsequent amplification of selected phage particles (containing single domain nanoantibody gene inside, and expressed single domain nanoantibody forming surface phage protein pIII) was repeated, as a rule, three times in series. All the manipulations were performed as described in publications of Tillib S. V., Ivanova T. I., Vasiliev L. A. 2010. Fingerprint analysis of nanoantibodies selection by phage display method using two variants of helper phages. Acta Naturae 2010; 2 (3): 100-108; Hamers-Casterman C., Atarhouch T., Muyldermans S. et al. Nature 1993; 363: 446-448; Nguyen V. K., Desmyter A., Muyldermans S. Adv. Immunol. 2001; 79: 261-296; Saerens D., Kinne J., Bosmans E., Wernery U., Muyldermans S., Conrath K. J Biol Chem. 2004; 279: 51965-51972; Rothbauer U., Zolghadr K., Tillib S., et al. Nature Methods 2006; 3: 887-889].

Figure 1:
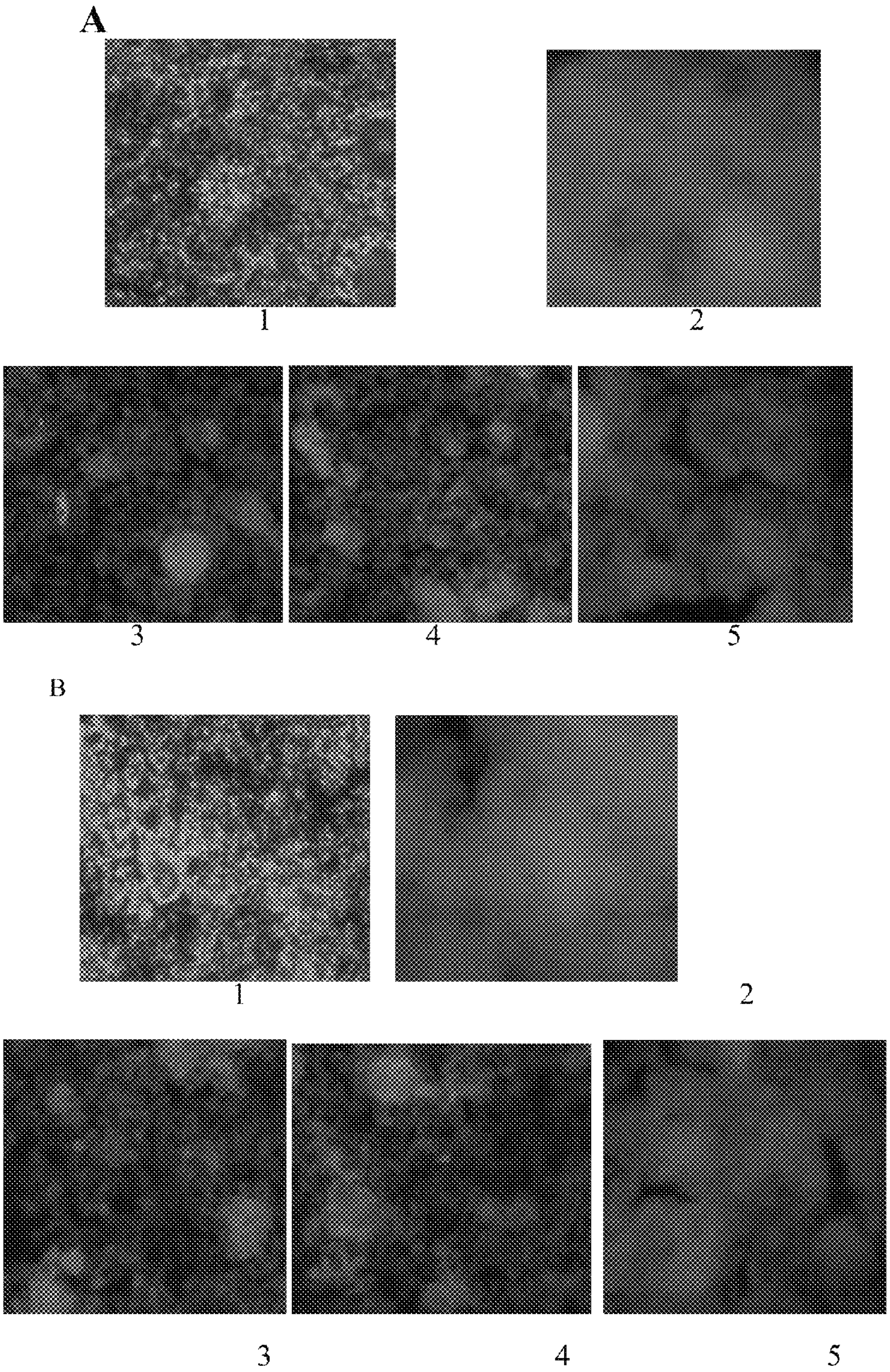
FIG. 1 shows the results of microimmunofluorescence (MIF) assay demonstrating specific binding of *C. trachomatis* by aCt1 and aCt2 nanoantibodies. Detection of bound nanoantibodies was performed using anti-HA antibodies of mice and secondary antibodies to immunoglobulins of mice, conjugated with fluorescein isothiocyanate (FITC). Specific binding is characterized with bright-green light. X 1500, where, A—photomicrography of MIF results with aCt1 (10 μ/ml)

Clones sequences of selected nanoantibodies were grouped according to similarity of their fingerprints, obtained during electrophoretic separation products of hydrolysis of amplified sequences of single domain nanoantibodies concurrently with three frequent-cutter restriction enzymes (HinfI, MspI, RsaI). cDNA sequences of nanoantibodies (SEQ ID NO: 1 and 3) were determined (FIG. 1). Hypervariable regions CDR1, CDR2 and CDR3 of antigen recognizing sequences of selected nanoantibodies (from left to right) were underlined in the designated sequences.

Nanoantibodies Production cDNA sequences of selected nanoantibodies were recloned into expression plasmid vector—modified pHEN6 vector [Conrath K E, Lauwereys M, Galleni M, Matagne A, Frere J M, Kinne J, Wyns L, Muyldermans S. Beta-lactamase inhibitors derived from single-domain antibody fragments elicited in the Camelidae. Antimicrob Agents Chemother. 2001; 45:2807-12] allowing attachment to C-end of (His)6-epitope nanoantibody (right after HA-epitope, encoded in pHEN6 vector). Owing to presence of signal peptide at the N-end of expressed sequence (pelB), developed recombinant protein (nanoantibody) accumulated in bacterial periplasm, facilitating efficient isolation by osmotic shock method without destruction of respective bacterial cells. Production of single domain nanoantibodies was performed in *E. coli* (BL21 strain). Expression was induced by adding 1 mM of indolyl-beta-D-galactopyranoside and the cells were incubated with vortexing during 7 hours at t=37oC or at night at t=29oC. Nanoantibody was isolated from periplasmatic extract using affinity chromatography in Ni-NTA-agarose using QIAExpressionist (QIAGEN, USA) purification system.

Demonstration of specificity of binding aCt1 and aCt2 nanoantibodies with *C. trachomatis.*

Ability of single domain nanoantibodies to specifically bind *C. trachomatis* antigens was tested using MIF assay with immobilized *C. trachomatis, C. pneumoniae, C. muridarum, C. psittaci* antigens under standard protocol (K. Persson, J. Boman. Comparison of Five Serologic Tests for Diagnosis of Acute Infections by *Chlamydia pneumoniae*. Clin. Diagn. Lab. Immunology, 2000, Vol. 7, No. 5, p. 739-740). (SUPPLEMENT 2) Wells with immobilized chicken ovalbumin protein were used as negative control (nonspecific protein). Detection of bound aCt1 H aCt2 was performed using murine anti-HA antibodies and secondary antibodies to murine immunoglobulins conjugated with fluorescein isothiocyanate (FITC). The results were evaluated by luminescent microscope with 1500× zoom. In case of specific antibodies binding with antigen bright-green light was observed.

FIG. 1 represents results, proving that nanoantibodies are specifically bound with immobilized *C. trachomatis* antigens, but not with *C. pneumoniae, C. muridarum, C. psittaci.*

A—photomicrography of MIF results with aCt1 (10 μ/ml)

Б—photomicrography of MIF results with aCt2 (10 μ/ml)

*C. trachomatis,* 2—ovalbumin protein, 3—*C. pneumoniae,* 4—C. muridarum, 5—*C. psittaci.*

In case of immobilized *C. trachomatis* antigen on fragments of Figure A1 and Б 1, bright-green light typical for FITC is observed, that is the evidence of positive reaction of aCt1 and aCt2 nanoantibodies binding with *C. trachomatis* cells. In case of other immobilized antigens (A3, A4, A5), negative control (A2) for aCt1 nanoantibodies, and also antigens (Б 3, Б 4, Б 5), negative control (Б 2) for nanoantibodies aCt2 the light is not observed. This is the evidence of binding failure of the selected nanoantibodies with antigens of *Chlamydia* of other species and failure of nonspecific binding with ovalbumin protein.

Example 4

Illustration of nanoantibodies binding aCt1 and aCt2 with eukaryotic cells, infected with *C. trachomatis* in vitro.

Eukaryotic culture of McCoy cells was infected with *C. trachomatis* under the standard method (Bashmakov Y K, Zigangirova N A, Pashko Y P, Kapotina L N, Petyaev I M. *Chlamydia trachomatis* growth inhibition and restoration of LDL-receptor level in HepG2 cells treated with mevastatin. Comp Hepatol., 2010, 28; 9:4). (SCHEDULE 3). Daily monolayer of cells was infected with *C. trachomatis* Bu-434 strain by application of *C. trachomatis* into cultural medium with subsequent centrifuging. Cells were incubated at 37° C. during 48 hours. Then the cells were fixed with acetone. Binding ability of aCt1 and aCt2 nanoantibodies with *C. trachomatis*, forming intracellular inclusions in eukaryotic cells, were tested by MIF assay under the standard protocol. Fixed uninfected cells were used as a control. Detection of bound aCt1 and aCt2 nanoantibodies was performed using murine anti-HA antibodies and secondary antibodies to murine immunoglobulins conjugated with fluorescein isothiocyanate (FITC). In case of specific binding of antibodies with *Chlamydia* in infected eukaryotic cells vacuoles, called inclusions containing *Chlamydia*, bright-green light was observed.

FIG. 2 represents results proving that single domain nanoantibodies specifically bind to *C. trachomatis*, forming intracellular inclusions in eukaryotic cells, and do not bind to uninfected cells.

McCoy cells, infected with *C. trachomatis* and dyed with aCt1 nanoantibodies—noninfected McCoy cells dyed with aCt1 nanoantibodies

3—McCoy cells, infected with *C. trachomatis* and dyed with aCt2 nanoantibodies

4—noninfected McCoy cells dyed with aCt2 nanoantibodies

Chlamydial inclusions inside of infected cells with bright-green light on fragments 1 and 3 are observed. There is no light in fragments 2 and 4 in uninfected cells. This proves specific binding of aCt1 and aCt2 nanoantibodies with *C. trachomatis* in cytoplasm of infected cells.

Thus, pharmaceutical products claimed in accordance with this invention proved their applicability for detection of *C. trachomatis* in vitro.

Example 5

Illustration of efficiency of inhibiting action of aCt1 and aCt2 nanoantibodies for development of *Chlamydia* infection.

To demonstrate inhibiting effect of nanoantibodies on development of *Chlamydia* infection in cell cultures, neutralizing effect of nanoantibodies on extracellular forms of *C. trachomatis* (elementary bodies) was evaluated. For this, nanoantibodies were diluted in PBS. *C. trachomatis* (105 CFU) were added to nanoantibodies dilutions and incubated at 37° C. for 45 minutes. Then preincubated elementary bodies were added to monolayer of McCoy cells, the cells were centrifuged for 1 hour at 1500 rpm and incubated for 48 hours in DMEM medium with cycloheximide (1 mg/ml). The cells were fixed with acetone, then dyed with monoclonal antibodies to MOMP protein of *C. trachomatis* conjugated with FITC adding Evans blue dye. The products were viewed by luminescence microscope under 1500× zoom. Chlamydial intracellular inclusions were detected as vacuoles with bright-green light at the red cells background.

FIG. 3 illustrates results of inhibiting effect analysis of aCt1 H aCt2 nanoanibodies on *C. trachomatis* in vitro in neutralization reaction of intracellular forms—elementary bodies of *Chlamydia.*

1—McCoy cells 48 hours after infection with *C. trachomatis* (control)

2—McCoy cells 48 hours after infection with *C. trachomatis*, preincubated with 1 μg/ml aCt1

3—McCoy cells 48 hours after infection with *C. trachomatis*, preincubated with 5 μg/ml aCt1

4—McCoy cells 48 hours after infection with *C. trachomatis*, preincubated with 10 μg/ml aCt1

5—McCoy cells 48 hours after infection with *C. trachomatis*, preincubated with 1 μg/ml aCt2

6—McCoy cells 48 hours after infection with *C. trachomatis*, preincubated with 5 μg/ml aCt2

7—McCoy cells 48 hours after infection with *C. trachomatis*, preincubated with 10 μg/ml aCt2

Large intracellular Chlamydial inclusions with bright-green light were detected in control substance in cells 48 hours after getting infected by *C. trachomatis*. In case of preincubation of elementary bodies *C. trachomatis* with aCt1 and aCt2 nanoantibodies, with nanoantibodies concentration 5 and 10 μg/ml, significant reduction of inclusions volume in cells monolayer, and also reduction of their size comparing to control were observed.

Thus, inhibiting action of aCt1 and aCt2 nanoantibodies on *C. trachomatis* intracellular development in vitro was illustrated.

Thus the examples with illustrations set forth prove performance of objective of this invention, i.e. isolation of new antibodies able to effectively bind antigens of *C. trachomatis* and inhibit development of *Chlamydia* infection. These new antibodies have the following advantages regarding prototype (classic monoclonal antibody): isolation, production and storage is more cost-efficient, effective and relatively simple; their size is significantly smaller, then in classic antibodies; they possess new structural features, allowing in principle to recognize some « hidden» for ordinary antibodies epitopes; properties of their compact structure must lead to relative simplicity of all the possible manipulations, adjustment to specific objectives, possibilities to create on their basis of various multivalent and multifunctional derivatives.

```
Sequence of the primary antibody aCt 1
                                        SEQ ID NO: 1
atggccctgcaggtgcagctggtggagtctgggggaggctcggtgcaggc

tggagggtctctgagactctcctgtacgacctctcactacgtcgccagta

actcctgcatggcctggttccgccaggctccggggaaaaagcgcgagggg

gtcgcaagtatcagccgtcgtgctgatatcacattctatgccgactccgt

gaaggaacgattcgtcatctcacgcgacaattccgagcgcacgctgtatc

tacaaatgaacagcctgaaacctgaggacactgccatgtactactgtgcg

gcagatctcagctactgcgggttgaccgaggagggctataatcactgggg

ccaggggacccaggtcaccgtctcctca
```

-continued

SEQ ID NO: 2

↓↓ ↓ malqvqlvesgggsvqaggslrlscttshyvasnscmawfrqapgkkreg

↓ vasisrraditfyadsvkerfvisrdnsertlylqmnslkpedtamyyca adlsycglteeqynhwgqgtqvtvss

Sequence of the primary antibody aCt 2

SEQ ID NO: 3 atggccctgcaggtgcagctggtggagtctggggggaggatcggtgcaggc tggaggctccctgagactgcactgtgcatcctctggatatgttgaagcta ggatcttgatgggctggttccgccaggctcccgggaaggagcgcgagggg -continued gtcgcggccatttatattggtgatggtactacagattatggcgactccgt gaagggccggttcaccgtctctcaagacggcgccaagaacgcgatctatc tgcacatgtacgacgtgaaacctgaggacgctgccacatactactgtgcg gcaggtattatgccttggtatcgaacgtggagcggaagactcaacgtggg tgactttgattcgtggggccaggggacccaggtcaccgtctcctca

SEQ ID NO: 4

↓↓ ↓ malqvqlvesgggsvqaggslrlhcassgyvearilmqwfrqapgkereg

↓ vaaiyigdgttdygdsvkgrftvsqdgaknaiylhmydvkpedaatyyca agimpwyrtwsgrlnvgdfdswgqgtqvtvss

What is claimed is:

1. A nanoantibody specifically binding to a surface antigen of *Chlamydia trachomatis*, the nanoantibody comprising the amino acid sequence SEQ ID NO: 2.

2. A nanoantibody specifically binding to a surface antigen of *Chlamydia trachomatis*, the nanoantibody comprising the amino acid sequence SEQ ID NO: 4.

3. The nanoantibody according to claim 1, wherein the nanoantibody inhibits a *Chlamydia* infection caused by *C. trachomatis*.

4. The nanoantibody according to claim 2, wherein the nanoantibody inhibits a *Chlamydia* infection caused by *C. trachomatis*.

5. A method of in vitro inhibiting a *Chlamydia* infection caused by *C. trachomatis*, the method comprising: pretreating elementary bodies of *C. trachomatis* by a therapeutically efficient amount of a nanoantibody specifically binding to a surface antigen of *Chlamydia trachomatis*, the nanoantibody comprising the amino acid sequence SEQ ID NO: 2; and adding the elementary bodies of *C. trachomatis* to target cells being infected.

6. A method of in vitro inhibiting a *Chlamydia* infection caused by *C. trachomatis*, the method comprising: pretreating elementary bodies of *C. trachomatis* by a therapeutically efficient amount of a nanoantibody specifically binding to a surface antigen of *Chlamydia trachomatis*, the nanoantibody comprising the amino acid sequence SEQ ID NO: 4; and adding the elementary bodies of *C. trachomatis* to target cells being infected.

* * * * *